United States Patent [19]

Nardella et al.

[11] 4,160,857
[45] Jul. 10, 1979

[54] CANISTER AND REMOVABLE BATTERY PACK UNIT THEREFOR

[75] Inventors: Paul C. Nardella, North Easton; Joseph D. Feeney, Carver; Thomas A. Wrublewski, Braintree; Anthony W. Gonsalves, Randolph, all of Mass.

[73] Assignee: Codman & Shurtleff, Inc., Randolph, Mass.

[21] Appl. No.: 878,493

[22] Filed: Feb. 16, 1978

[51] Int. Cl.² .............................................. H01M 2/10
[52] U.S. Cl. ........................................ 429/97; 429/99
[58] Field of Search ........................... 429/97, 99, 1, 9

[56] References Cited

U.S. PATENT DOCUMENTS

| 1,075,556 | 10/1913 | Fenoughty | 429/99 |
| 3,829,332 | 8/1974 | Iizuka et al. | 429/97 |
| 3,887,393 | 6/1975 | LaRue | 429/99 |
| 3,963,972 | 6/1976 | Todd | 429/97 |

FOREIGN PATENT DOCUMENTS

| 362152 | 9/1929 | Fed. Rep. of Germany | 429/97 |
| 375333 | 10/1939 | Italy | 429/97 |

*Primary Examiner*—Donald L. Walton
*Attorney, Agent, or Firm*—Richard J. Rodrick

[57] ABSTRACT

A canister for a removable battery comprises a receptacle for receiving the battery therein. The battery is insertable so that its electrical terminals are upwardly facing and exposed for contact. A cover is provided for enclosing the battery in the receptacle and electrical contacts are associated with the cover for contacting the battery terminals when the cover is positioned over the receptacle with the battery inside. An electrical connector is electrically connected to the electrical contacts inside the cover and provides means on the outside of the cover for an electrical connection in order to derive voltage from the battery.

A battery pack unit in combination with the canister comprises a plurality of batteries electrically connected to each other and has electrical terminals in contact with the electrical contacts in the cover. The terminals are electrically connected to the batteries in order to provide a source of electrical current from the pack unit.

A further combination includes the canister and battery pack unit together with a tool electrically operated by direct current with a cable connecting the canister with the tool for providing direct current from the battery unit in the canister to the tool for driving the same.

5 Claims, 6 Drawing Figures

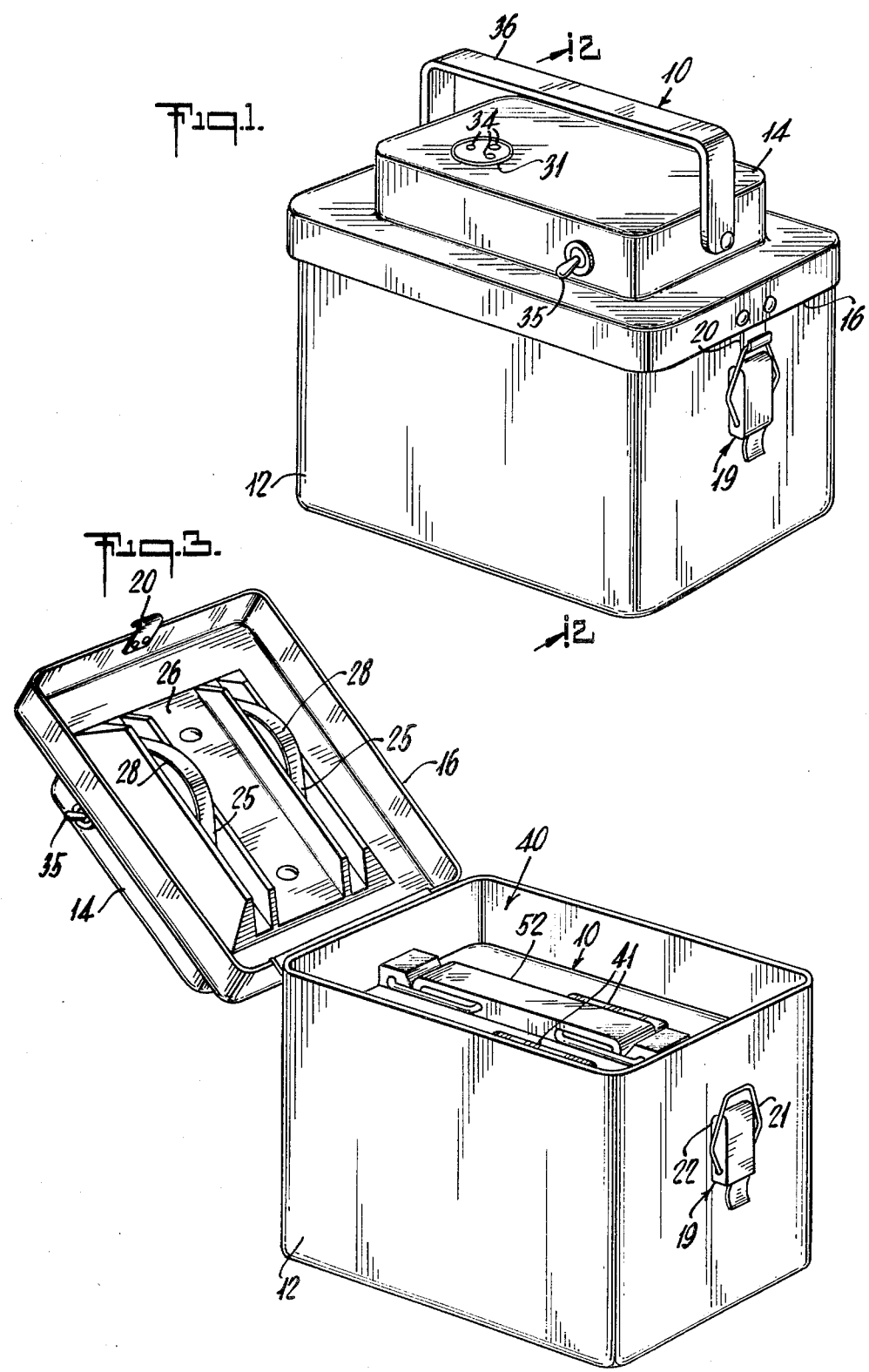

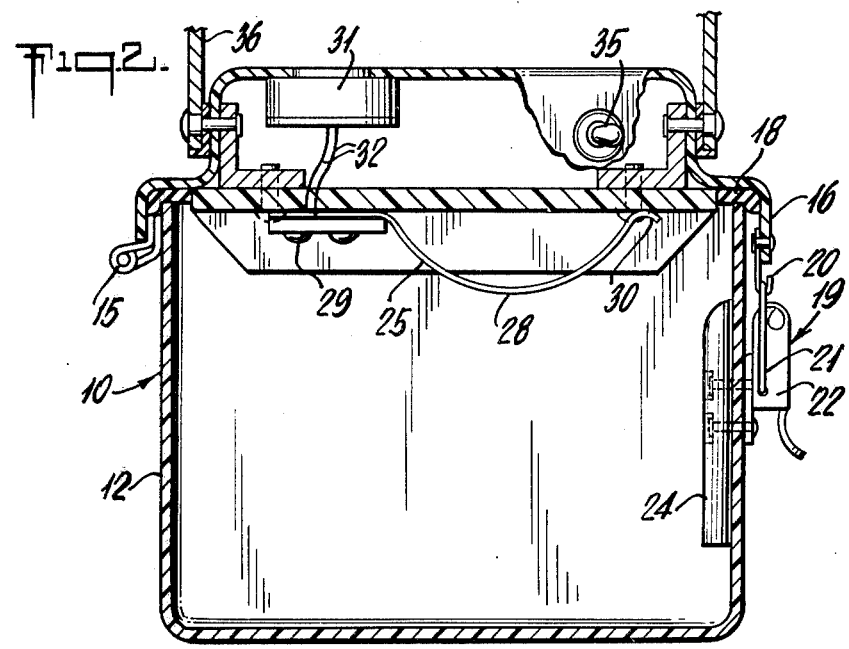
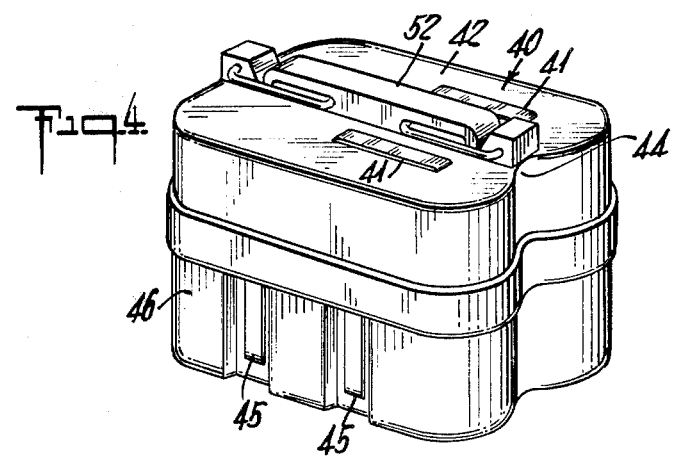
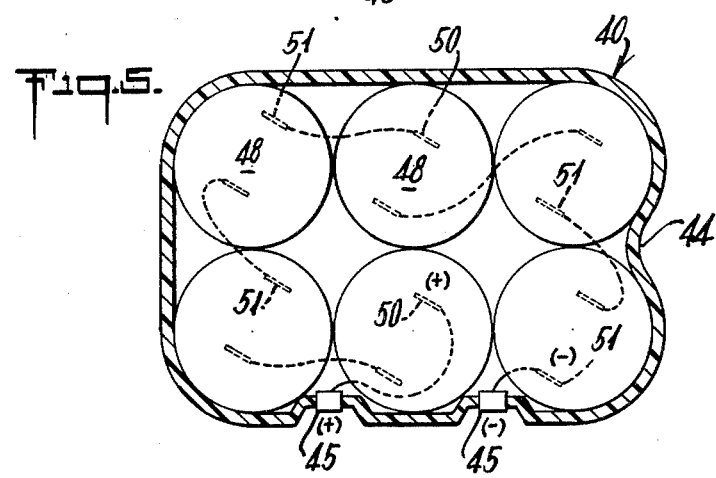

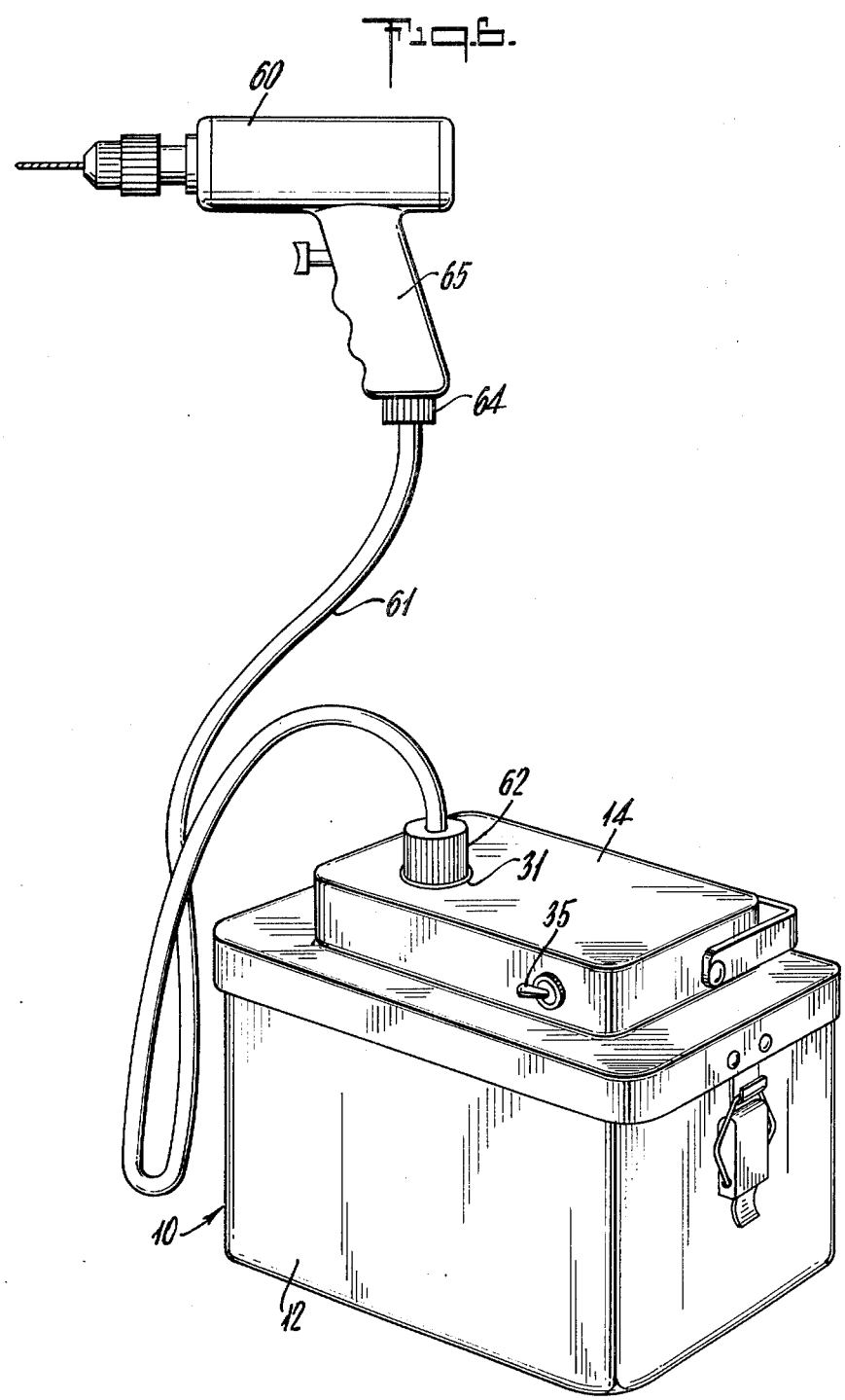

CANISTER AND REMOVABLE BATTERY PACK UNIT THEREFOR

BACKGROUND OF THE INVENTION

The present invention relates to a canister for holding a removable battery therein with connection means to derive current from the battery, and, more particularly, concerns a removable battery pack unit in a canister which provides an electrical connection to that unit. The present invention further relates to a canister with a removable battery pack unit therein in combination with a tool electrically operated by direct current which is provided by the battery pack unit.

Many electrically operated surgical tools are being designed to perform under direct current rather than alternating current in the operating rooms of hospitals and the like. Use of anesthesia during surgery complicates the use of electrically operated tools inasmuch as an inadvertent spark may cause the anesthesia to ignite. With this in mind battery powered surgical tools, such as drivers for drills, saws, reamers and the like, have become more prominent. In addition to the necessity of sometimes providing large amounts of direct current for tools which, for example, must drill through bone structure, the battery should also be sterilized to be compatible with its inclusion in the clean operating area. Most commonly used batteries for use with electrically operated surgical tools, such as the rechargeable secondary cell type, and particularly, sealed lead-acid cells, are not sterilizable in their normal condition inasmuch as the autoclaving process or similar sterilization process may cause the battery to weaken or produce other defects. Accordingly, it is desirable to provide a container for a battery which can be sterilized, and also a container which can include a battery or a number of batteries with sufficient energy required to drive electrically operated surgical tools.

In U.S. Pat. No. 2,861,578, there is disclosed a utility cabinet assembly, preferably directed for manicuring purposes, which includes an electrically powered manicure implement and a portable carrying cabinet therefor in which there is stored an electrical power supply for the implement. This type of utility assembly does not meet the above defined requirements for a container to hold a battery which can be used in a clean surgical operating area.

It is also desirable to employ batteries of the secondary cell type which are rechargeable since the electrically operated tools drain a considerable amount of energy during their use. A rechargeable battery pack unit and a battery charger are disclosed in the applicant's co-pending patent application Ser. No. 878,494 filed on even date with this application, the specific battery pack unit disclosed therein being adaptable for inclusion in a container which meets the requirements set forth above.

SUMMARY OF THE INVENTION

A canister for a removable battery comprises a receptacle for receiving the battery therein. The battery is insertable so that its electrical terminals are upwardly facing and exposed for contact. A cover is provided for enclosing the battery in the receptacle. There are electrical contacts associated with the cover for contact with the battery terminals when the cover is positioned over the receptacle with the battery therein. An electrical connector is connected to the electrical contacts inside the cover and it provides means on the outside of the cover for an electrical connection in order to derive voltage from the battery.

In the preferred embodiment of the canister of the present invention, the cover is hingedly attached to the receptacle and a resilient gasket is provided for location between the cover and the receptacle so that the canister is capable of being sterilized for use in clean areas. A pair of spring-resilient metallic strips serve as the electrical contacts mounted inside the cover and are arranged to springably contact the terminals of the battery when the cover is positioned over the receptacle with the battery inside. One of the strips will contact the negative terminal, the other will contact the positive terminal. Latching means is provided for maintaining the cover in a closed position on the receptacle. There is also included in the preferable embodiment a switch mounted in the cover and operable from the outside surface thereof. This switch is adapted to interrupt the flow of electrical current from the battery to the connector when in the off position, and adapted to allow current to flow from the battery to the connector when in the on position.

Another aspect of the present invention is a combined canister and removable battery pack unit, the canister being substantially as described above. The battery pack unit comprises a plurality of batteries electrically connected to each other and has electrical terminals in contact with the electrical contacts of the canister. The terminals are electrically connected to the batteries in order to provide a means of deriving energy from the pack unit. Preferably, the pack unit has a pair of metallic strips on an upper surface thereof to serve as the terminals for contacting the electrical contacts in the cover. In addition, the batteries are preferably secondary, rechargeable cells.

A further aspect of the present invention is a combined canister removably enclosing a battery pack unit therein, the canister having means associated therewith for making electrical contact with the pack unit. An electrical connector is included on the outside surface of the canister to provide energy from the pack unit. This pack unit comprises a plurality of batteries electrically connected to each other. These elements are combined with a tool electrically operated by direct current and a cable connected at one end to the tool and at its other end to the connector on the canister, the cable providing a flow of direct current from the battery unit in the canister to the tool for driving the same.

BRIEF DESCRIPTION OF THE DRAWINGS

FIG. 1 is a perspective view illustrating the preferred canister of the present invention in the closed position;

FIG. 2 is a cross-sectional view taken along lines 2—2 of FIG. 1;

FIG. 3 is a perspective view illustrating the preferred canister of the present invention in the open position with the preferred battery pack unit therein;

FIG. 4 is a perspective view illustrating the preferred battery pack unit of the present invention;

FIG. 5 is a plan view of the preferred battery pack unit with its cover removed for viewing of the batteries and electrical connections inside; and FIG. 6 is a perspective view illustrating the preferred canister and battery pack unit assembly together with an electrically operated tool, electrically connected to the canister.

DETAILED DESCRIPTION

While this invention is satisfied by embodiments in many different forms there is shown in the drawings and will be herein described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Referring to the drawings, particularly to FIGS. 1 and 2, there is illustrated a canister 10. Canister 10 is comprised of a receptacle 12 which is generally a boxlike container preferably of a rectangular cross-section. Receptacle 12 is constructed to have four walls and a bottom surface, with its top portion being open so that the battery may be inserted therein. A one-piece receptacle 12 is preferably employed inasmuch as this is often conveniently fabricated. Canister 10 further includes a cover 14 which is mounted atop receptacle 12 by a hinge 15 so that cover 14 may swing open for access to the inside of receptacle 12. Cover 14 is preferably provided with an overlapping lip 16 so that a resilient gasket 18, such as rubber or the like, may be located at the top of receptacle 12 between the receptacle and cover 14. Lip 16 assists in positioning gasket 18 and holding the same in place when the cover is closed on the receptacle. To also assist in keeping cover 14 closed on receptacle 12 a latching device 19 is included on the canister. This latching device includes a hook 20 attached to cover 14 and a ring 21 freely connected to a bracket 22 which is mounted on the wall of receptacle 12. Once ring 21 is slipped over hook 20, bracket 22 is operable to be pushed inwardly in order to render ring 21 taut on hook 20. This arrangement serves to maintain cover 14 closed against receptacle 12, and together with gasket 18 provides a tight seal. Accordingly, this arrangement provides a sufficient container assembly for sterilization purposes since the contents of the receptacle inside are unaffected by the sterilization process.

On the inside surface of the same wall of receptacle 12 opposite from latching device 19, there is a guiding key 24. This guiding key is merely to assure that the particular type battery pack unit, preferably adaptable for reception in canister 10, is insertable in the proper orientation. A provision is included on the battery pack unit to matingly correspond with guiding key 24, as will hereinafter be described.

In FIGS. 2 and 3 it can be seen that a pair of spring-resilient metallic strips 25 are mounted inside cover 14. An electrically non-conductive mounting pad 26 serves as a support member for strips 25 and also to electrically isolate the strips. Strips 25 are formed to include a smoothly curved raised portion 28; curved portion 28 protrudes downwardly and is the portion of the metallic strip which contacts the terminals on the battery pack unit. Metallic strips are connected at one end 29 to mounting pad 26, whereas the other end 30 of the strip is free thereby allowing curved portion 28 to flexibly compress during contact with the terminals of the battery unit when the cover is positioned over the receptacle with that unit therein.

An electrical connector 31 is mounted in cover 14. Inside cover 14 connector 31 makes a connection with metallic strips 25 by appropriate wiring means 32. The wires are connected to female pegs 34 in connector 31 which are accessible on the outside surface of cover 14.

A mating plug device is conveniently plugged into female peg 34 in order to make the electrical connection to the canister for deriving voltage from the battery. In addition, a toggle switch 35, or similar switch operable from the outside of the canister, is mounted in the cover 14. By appropriate electrical wiring (not shown, but well known) switch 35 is adapted to interrupt the flow of electrical current from the battery inside receptacle 12 to connector 31 when in the off position, and adapted to allow current to flow from the battery to connector 31 when in the on position. This, of course, provides a measure of control during use of the canister-battery assembly, such as, for example, eliminating unnecessary drain of the battery when the tool is not being used.

A handle 36 is optionally attached to cover 14 to provide a convenient means to lift the canister.

Turning now to FIG. 3, canister 10 is illustrated in the open position so that cover 14 is swung back to allow access to receptacle 12. The preferred battery pack unit 40 is shown inserted in receptacle 12 so that its electrical, metallic terminals 41, on the upper surface 42 of unit 40, are upwardly facing and exposed for contact with metallic strips 25 and particularly curved portion 28. It can be seen that, in this preferable embodiment, there is mating alignment between electrical contacts 25 in the cover and electrical terminals 41 on the battery unit to assure positive contact when the cover is closed over the receptacle. It is noted that battery pack unit 40 has an indentation 44 on one of its end surfaces; this indentation mates with guiding key 24 in receptacle 12 so that pack unit 40 may be properly inserted in the correct orientation in the receptacle.

Adverting now to FIGS. 4 and 5, the preferred battery pack unit 40 is illustrated. This pack unit is also, and in more detail, described in the co-pending patent application filed even date herewith, but the pertinent components of the pack unit will be pointed out herein. In addition to terminals 41 on upper portion 42, there is also another pair of metallic strips 45 on a side portion 46 of the battery pack unit; these side terminals 45 allow pack unit 40 to be recharged in the particular type battery charger described in said co-pending patent application. Inside pack unit 40 are a plurality of batteries 48, such as the secondary, rechargeable cell type, particularly sealed lead-acid cells. Each battery 48 has a positive terminal 50 and a negative terminal 51. The batteries are electrically connected, by appropriate wiring, to each other, generally positive terminal 50 of one battery to negative terminal 51 of adjacent battery. A positive terminal 50 on one battery and a negative terminal 51 on another battery are left free for connection to the pack unit terminals 41 and 45. Accordingly, one of the metallic strips 41 on the battery unit is a negative terminal, while the other of the metallic strips 41 is a positive terminal. A handle 52 is included on battery pack unit 40 for conveniently lifting the unit in and out of receptacle 12.

While the canister may be fabricated from many different materials, a light weight metal such as aluminum, for strength purposes and for withstanding sterilization processes, is preferred. In order to hold a battery pack unit such as described herein, typical dimensions of the overall canister, including cover and receptacle, are 6½ by 4½ by 5¾ inches high (16.5 by 11.5 by 14.5 cm.).

Referring now to FIG. 6, canister 10 is illustrated in its mode of use in conjunction with a tool 60 which is electrically operated by direct current. Although not shown because the cover 14 is sealably closed over receptacle 12, the preferred battery pack unit is incorporated inside the canister. A cable 61 includes a connector 62 at one end, this connector is adapted to mate with connector 31 on cover 14 of the canister. This, in turn, allows energy to be derived from the battery unit within, since connector 31 is in electrical contact with that unit. The other end of cable 61 has another connector 64 which is adapted to mate with a corresponding electrical connection on the tool 60, in this instance on the handle portion 65 thereof. Accordingly, as soon as toggle switch 35 is flipped to the on position, direct current flows from canister 12 through cable 61 and into electrically operated tool 60. This tool may be any number of tools preferably employed for surgical purposes, including, but not limited to, hand-held drivers for use in surgical operations such as drills, saws, reamers and the like.

Thus, the present invention provides a canister particularly suitable for receiving and holding a removable battery pack unit, particularly of the rechargeable type, which can be sealably closed and sufficiently sterilized to be used in clean areas such as hospital operating rooms. The canister-battery pack unit assembly provides the energy for electrically operated tools driven by direct current, the battery pack unit being accessible for recharge when its energy level becomes diminished by use of the tool.

What is claimed is:

1. In combination, a canister and a removable battery pack unit, said canister comprising a receptacle into which said battery pack unit is positioned; a cover enclosing said battery pack unit in said receptacle; a pair of electrical spring contacts located on the inside of said cover projecting downwardly for contact with said battery pack unit; an electrical connector in said cover electrically connected to said electrical spring contacts, said connector providing means on the outside of said cover for an electrical connection in order to derive voltage from said battery pack unit; and said pack unit comprising a plurality of batteries electrically connected to each other, said batteries enclosed in a housing which includes two pairs of metallic strips serving as electrical contacts, both pairs of strips electrically connected to said batteries so that one of said strips in each pair is a negative terminal and the other of said strips in each pair is a positive terminal, one pair of metallic strips located in a side portion of said housing and not making electrical contacts with said receptacle, the other pair of metallic strips located in the upper portion of said housing and adapted to be contacted by said spring contacts when said cover is closed to thereby provide a means of deriving energy from said pack unit.

2. A combination as defined in claim 1 wherein said battery pack unit further includes a handle on its upper surface for lifting the unit in and out of the receptacle, said handle positioned between the metallic strips on the upper surface of the battery pack unit housing.

3. A combination as defined in claim 1 which further includes a tool electrically operated by a direct current and a cable connected at one end to said tool and at the other end to said connector on said canister, said cable providing a flow of direct current from said battery unit in said canister to said tool for driving the same.

4. A combination as defined in claim 3 wherein said tool is a hand-held driver for use in surgical operations.

5. A combination as defined in claim 1 wherein said batteries in said pack unit are secondary, rechargeable cells.

* * * * *